US006979420B2

(12) United States Patent
Weber

(10) Patent No.: US 6,979,420 B2
(45) Date of Patent: Dec. 27, 2005

(54) METHOD OF MOLDING BALLOON CATHETERS EMPLOYING MICROWAVE ENERGY

(75) Inventor: Jan Weber, Maple Grove, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/109,220

(22) Filed: Mar. 28, 2002

(65) Prior Publication Data

US 2003/0183967 A1    Oct. 2, 2003

(51) Int. Cl.[7] .............................................. B29C 49/64
(52) U.S. Cl. ...................... 264/521; 264/523; 264/528
(58) Field of Search ................................. 264/454, 520, 264/521, 523, 528

(56) References Cited

U.S. PATENT DOCUMENTS

| 2,863,174 | A |   | 12/1958 | Schuman et al. |
| 3,874,207 | A |   | 4/1975  | Lemelson |
| 3,957,943 | A |   | 5/1976  | Ogura |
| 4,003,554 | A |   | 1/1977  | Chauffoureaux |
| 4,035,598 | A | * | 7/1977  | Van Amsterdam .......... 219/697 |
| 4,040,162 | A |   | 8/1977  | Isogai et al. |
| 4,093,484 | A |   | 6/1978  | Harrison et al. |
| 4,143,112 | A |   | 3/1979  | Turner |
| 4,298,324 | A |   | 11/1981 | Soulier |
| 4,339,295 | A |   | 7/1982  | Boretos et al. |
| 4,390,482 | A |   | 6/1983  | Feurer |
| 4,407,651 | A |   | 10/1983 | Beck et al. |
| 4,568,262 | A |   | 2/1986  | Feurer |
| 4,671,757 | A |   | 6/1987  | Volk, Jr. |
| 4,760,228 | A | * | 7/1988  | Kudo .......................... 219/686 |
| 4,859,380 | A |   | 8/1989  | Ogata |
| 4,950,239 | A |   | 8/1990  | Gahara et al. |
| 5,104,593 | A | * | 4/1992  | Joseph ........................ 264/407 |
| 5,222,543 | A | * | 6/1993  | Carlstrom et al. .......... 164/114 |
| 5,324,345 | A | * | 6/1994  | Rutjes et al. .................. 65/64 |
| 5,421,832 | A |   | 6/1995  | Lefebvre |
| 5,496,311 | A |   | 3/1996  | Abele et al. |
| 5,622,665 | A |   | 4/1997  | Wang |
| 5,628,950 | A |   | 5/1997  | Schrenk et al. |
| 5,641,423 | A |   | 6/1997  | Bridges et al. |
| 5,653,778 | A |   | 8/1997  | Rutjes et al. |

(Continued)

FOREIGN PATENT DOCUMENTS

WO    WO 00/64608    11/2000

(Continued)

OTHER PUBLICATIONS

International Search Report; PCT US 03/01203, reported dated Jun. 4, 2003.

(Continued)

Primary Examiner—Michael P. Colaianni
Assistant Examiner—Monica A. Fontaine
(74) Attorney, Agent, or Firm—Marshall, Gerstein & Borun LLP

(57) ABSTRACT

An apparatus for molding balloon catheters is disclosed. The balloon may be molded by providing a polymeric tube within a mold having an interior cavity in the shape of the desired balloon. Microwave energy, which may be generated by a gyrotron, may then be directed toward the mold, to heat the polymeric material without heating the mold. Once heated, pressurized fluid may be injected into the tube to blow the polymeric material against the interior cavity whereupon the material can cool to form the balloon or can be further heatset by additional microwave energy and be cooled to form the balloon.

19 Claims, 4 Drawing Sheets

U.S. PATENT DOCUMENTS

| | | | |
|---|---|---|---|
| 5,762,972 | A | 6/1998 | Byon |
| 5,773,042 | A | 6/1998 | Amano et al. |
| 5,775,338 | A | 7/1998 | Hastings |
| 5,844,217 | A | 12/1998 | Hawley et al. |
| 5,948,194 | A | 9/1999 | Hill et al. |
| 5,951,513 | A * | 9/1999 | Miraki ............ 604/96.01 |
| 6,004,289 | A * | 12/1999 | Saab ............ 604/96.01 |
| 6,190,355 | B1 | 2/2001 | Hastings |
| 6,270,707 | B1 | 8/2001 | Hori et al. |
| 6,368,994 | B1 * | 4/2002 | Sklyarevich ............ 502/5 |
| 6,478,911 | B1 * | 11/2002 | Wang et al. ............ 156/109 |
| 6,696,121 | B2 * | 2/2004 | Jung, Jr. et al. ............ 428/35.7 |
| 2001/0054775 | A1 * | 12/2001 | Nandu et al. ............ 264/1.36 |

FOREIGN PATENT DOCUMENTS

| | | |
|---|---|---|
| WO | WO 01/51115 | 7/2001 |

OTHER PUBLICATIONS

Pages from Farlow's Scientific Glassblowing Inc.'s website.
International Search Report from PCT/US2004/000848 application; report dated Jun. 4, 2004.

* cited by examiner

METHOD OF MOLDING BALLOON CATHETERS EMPLOYING MICROWAVE ENERGY

FIELD OF THE DISCLOSURE

The disclosure generally relates to balloon catheters and, more particularly, relates to methods of manufacturing balloon catheters.

BACKGROUND OF THE DISCLOSURE

Angioplasty is an effective medical procedure performed to expand constricted sections of blood vessels. In such a procedure, an angioplasty balloon or balloon catheter is navigated to the site of the constriction. The balloon is inflated upon reaching the site, by way of fluid pressure injected into the balloon, to thereby expand its dimension. The expansion of the balloon exerts pressure on the vessel walls to thereby widen the vessel and alleviate constriction to blood flow.

Conventionally, such balloons are manufactured from a polymeric material and are molded in a blow molding procedure. More specifically, a cylinder or tube of polymeric material, known as a parison, is placed within a mold having an interior cavity in the desired shape of the balloon. The mold is then heated, with the heat of the mold being conducted to the parison, such that upon introduction of fluid pressure into the parison the polymeric material deforms into the shape of the mold cavity. The mold is then cooled to cause the polymeric material to harden into the shape of the mold.

Typically, the mold is provided in a clam shell design wherein each half of the mold includes half of the interior cavity forming the balloon. The mold can therefore be wrapped around the parison and easily removed to facilitate production. The parison itself can be heated by immersing the entire mold within a hot water, oil, glycerin or other fluid bath and allowing the mold and parison to be heated via conduction. One problem associated with such a process is that heating of the parison is less than optimal. Heating via conduction, by its very nature, is a relatively slow process. Moreover, the tubular shape of the parison lends itself toward a substantial heat flow axially along the parison which itself tends to heat portions of the polymeric material at which balloon deformation is not desired. Accordingly, such systems typically need to employ some sort of cooling mechanism, such as a cold air jet, to keep the areas of the parison, outside of the mold, cool. One problem stemming from such a system is that temperature control or distribution across the entire polymeric tube is difficult. For bigger balloon sizes, in which the gap between the polymeric tube and mold wall is too large to give sufficiently fast transfer of heat, small amounts of water are often injected inside the mold between the parison and the mold for better heat conduction.

Moreover, with such conventional systems, it is not possible to heat different axial sections of the polymeric tube to different temperatures. For example, this may be advantageous when it is desired to create different physical properties within the balloon itself such as multiple areas of varying diameter, wall thickness, or multiple areas consisting of different materials to be heated to different temperatures. Although a section of the mold can be kept above the fluid bath, having the effect of a cooler section in the mold, still because of the slow heating process, a sharp temperature transition is not possible. It is also not possible to set the metal mold to a different temperature than that to which the polymeric tube is heated. The mold must therefore be cooled down before the balloon can be removed.

SUMMARY OF THE DISCLOSURE

In accordance with one aspect of the disclosure, a method of molding balloon catheters is provided which comprises the steps of positioning a cylinder of polymeric material within a mold, the mold having an interior cavity, heating the cylinder of polymeric material using microwave energy, and injecting fluid pressure into an interior of the cylinder of polymeric material with the fluid pressure expanding the cylinder into the interior cavity of the mold.

In accordance with another aspect of the disclosure, a balloon catheter molding apparatus is provided which comprises a microwave source, a mold, and a fluid pressure source. The microwave source is adapted to emit a microwave band, while the mold is positioned proximate to the microwave band. The fluid pressure source is operatively associated with the mold and adapted to direct pressurized fluid through a polymer tube positioned within the mold.

In accordance with another aspect of the disclosure, a balloon catheter molding apparatus is provided which comprises a gyrotron, a mold, a waveguide, and at least one lens. The gyrotron is adapted to generate microwave radiation, while the mold includes a cavity adapted to receive a parison. The waveguide is positioned to transmit the microwave radiation from the gyrotron to the mold. The lens is adapted to focus the microwave radiation onto the mold.

These and other aspects and features of the disclosure will become more apparent upon reading the following detailed description when taken in conjunction with the accompanying drawings.

Figure 1:
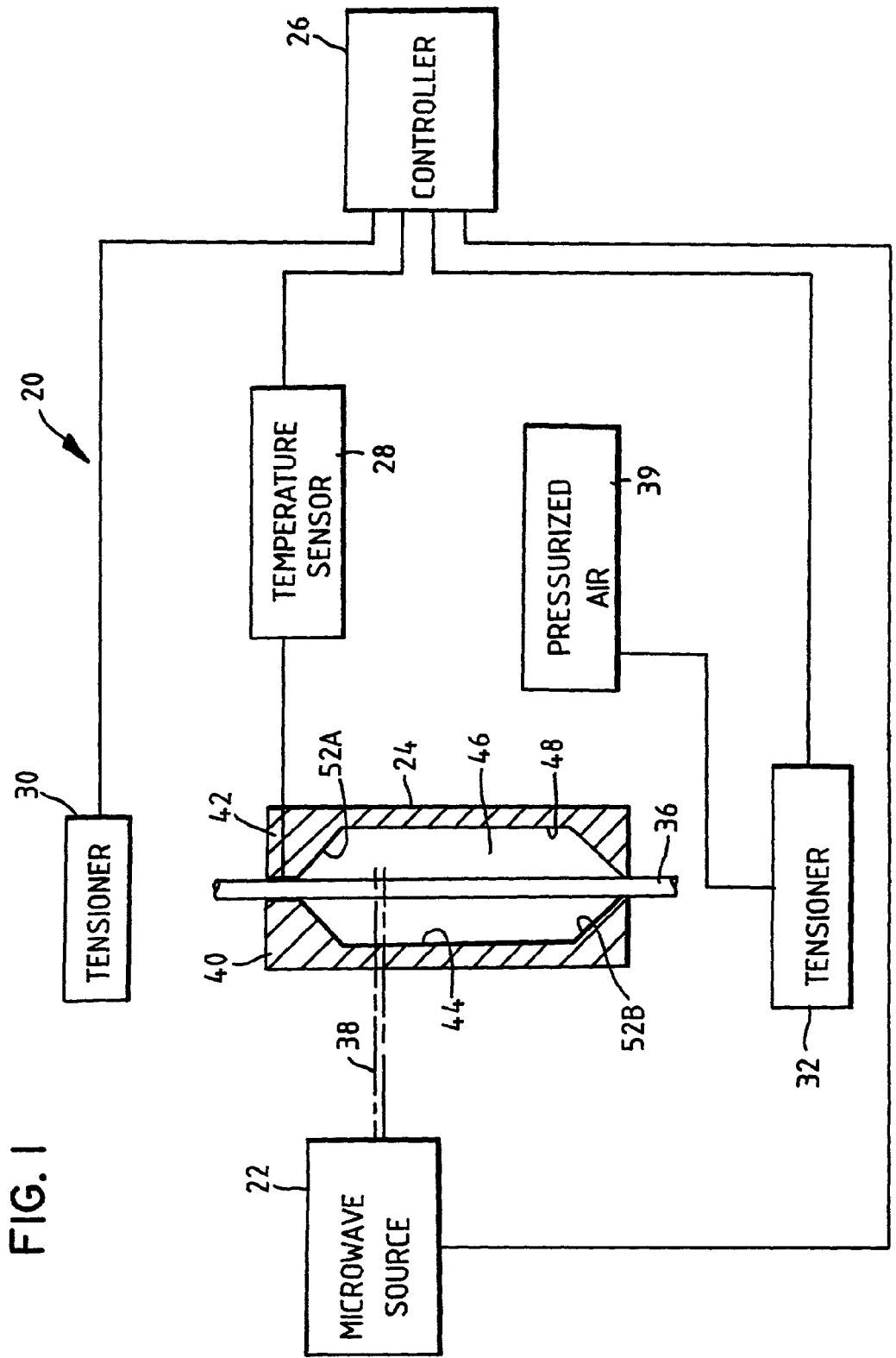
FIG. 1 is a block diagram of a balloon catheter molding apparatus constructed in accordance with the teachings of the disclosure.

While the disclosure is susceptible to various modifications and alternative constructions, certain illustrative embodiments thereof have been shown in the drawings and will be described below in detail. It should be understood, however, that there is no intention to limit the disclosure to the specific examples disclosed, but on the contrary, the intention is to cover all modifications, alternative constructions, and equivalents falling within the spirit and scope of the invention as defined by the appended claims.

DETAILED DESCRIPTION OF THE DISCLOSURE

Referring now to the drawings, and with specific reference to FIG. 1, a balloon catheter molding apparatus, constructed in accordance with the teachings of the disclosure, is generally referred to by reference numeral 20. As described herein, the apparatus 20 may be advantageously employed for the manufacture of balloon catheters and angioplasty balloons, but can be employed in conjunction with many other types of polymeric devices including, but not limited to, other medical devices such as contact lenses and the like.

Figure 3:
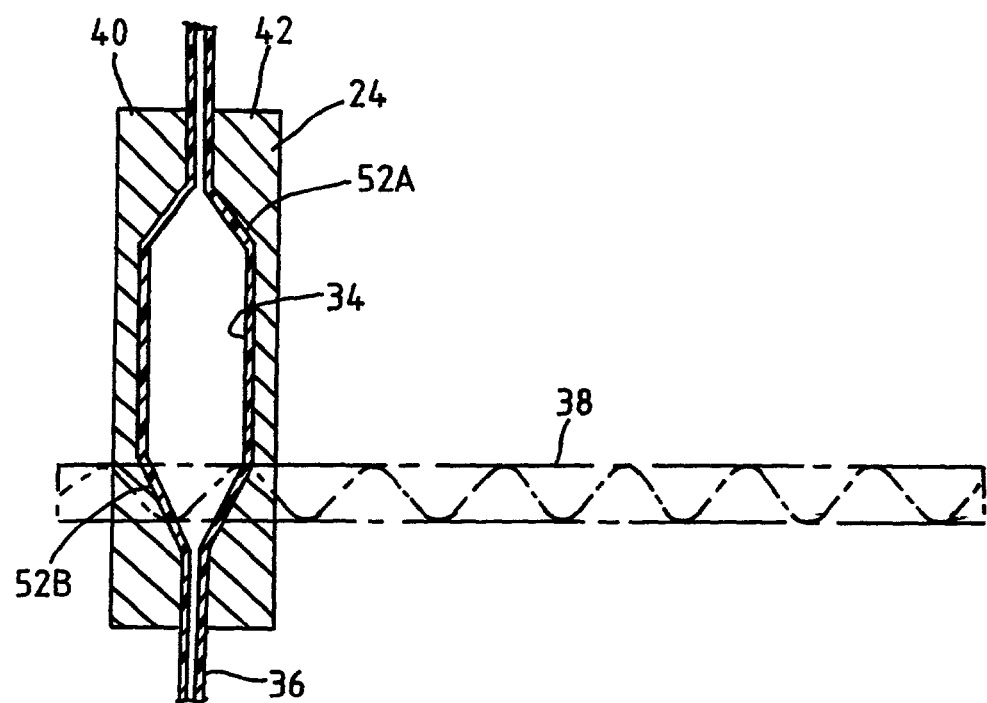
FIG. 3 is a schematic representation of one embodiment of a molding apparatus constructed in accordance with the teachings of the disclosure.

Referring again to FIG. 1, the system 20 may include a source of microwave energy 22, a mold 24, a controller or processor 26, a temperature sensor 28 and first and second tensioners 30, 32. Employing such elements, the apparatus 20 can form a balloon 34 from a work piece or parison 36. More specifically, the parison 36, which may be provided in the form of a tube or cylinder of polymeric material, is provided within the mold 24. The source of microwave energy 22 then directs a beam or band 38 of microwave energy toward the mold 24, with the microwave energy heating the polymeric material. Once heated or during heating, pressurized fluid, which may be provided in the form of compressed air from a compressor 39, is injected through the workpiece 36 causing a portion of the workpiece 36 within the mold 24 and heated by the microwave source 22, to expand within the mold 24 as shown best in FIG. 3.

Figure 2:
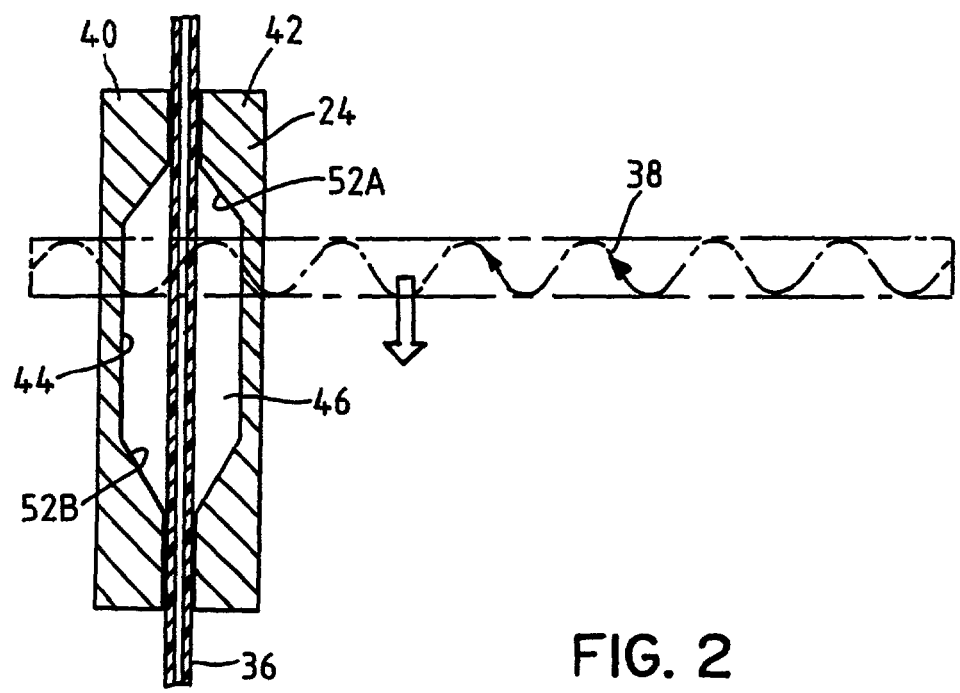
FIG. 2 is a diagrammatic cross-sectional view of a mold and molding process constructed in accordance with the teachings of the disclosure.

Referring now to FIG. 2, the mold 24 is shown in further detail. While it is to be understood that the mold 24 may be provided in a variety of forms, one workable embodiment provides the mold 24 in the form of a clam shell mold having first and second complementary halves 40, 42 with each half 40, 42 having a recess 44 which, when combined, forms the entire mold cavity 46. The cavity 46 is shaped to the desired profile 48 of the balloon 34. In the depicted embodiment, each recess 44 includes a cylindrical outer surface 48 as well as top and bottom canted or conical surfaces 52a, 52b.

Preferably, the mold 24 is manufactured from a microwave-transparent material having a low dielectric loss characteristic, such as a ceramic material or quartz material, although many other types of non-metallic materials, including but not limited to Teflon®, or boron nitride, can be employed with similar efficacy. If the mold 24 is made of Teflon®, for example, or another microwave transparent material that is a poor thermal conductor, application of the microwave beam will allow the temperature of the balloon to be raised to the heatset temperature by applying further microwave energy after the balloon has been blown.

Figure 6:
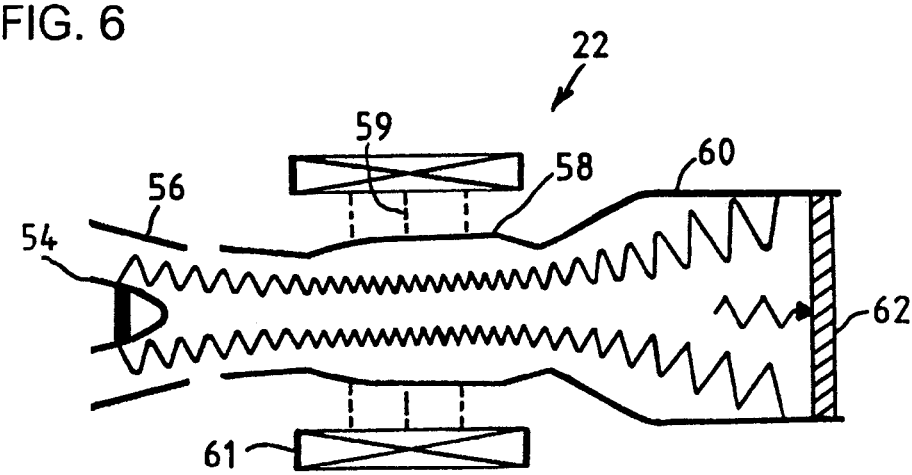
FIG. 6 is a schematic representation of a gyrotron.

With regard to the microwave source 22, it may be provided in the form of a gyrotron adapted to emit microwave energy at a frequency within the range of 10 gigahertz to 110 gigahertz, and a wavelength within the range of 2.7 mm to 30 mm. As shown in FIG. 6, the gyrotron may consist of an electron gun having a cathode 54, an anode 56, a resonance chamber 58 immersed in a strong magnetic field 59, and a collector 60. The magnetic field 59 may be generated by superconducting magnets or solenoids 61. When the cathode 54 is energized, accelerating electrons emitted thereby enter the magnetic field 59 and start to spiral, or gyrate, at a high relativistic speed and in very small loops. An advantage of using microwave energy as opposed to, for example, infrared, is the tremendous speed of heating that is attainable due to the matching wavelength of the microwave in respect to the heated object.

For example, using a magnetron injection-type electron gun with the cathode 54 potential at ten kilovolts and a magnetic field 59 of twelve Tesla will result in the electrons being gyrated in a spiral with a radius of 30 micrometers and a cyclotron frequency of 330 GHz. Changing the magnetic field 59 enables the frequency to be changed accordingly. In order to obtain a high frequency wave, the resonant cavity should be designed in such a way that its geometric size matches a harmonic of the wavelengths created by the gyrating electrons. The electromagnetics transmitted through the radio frequency (RF) window 62, and by means of a waveguide 63, can be transported to the target. Manufacturers of gyrotron systems deliver such gyrotrons with built-in mode converters to convert the beam to a gaussian-shaped He11 mode, which can be guided through a circular wave guide with low loss. For example, Insight Product Company of Brighton, Mass. provides such a system. The He11 mode radiated from an open-ended circular waveguide has an axisymmetric narrow Gaussian beam with well-defined polarization and direction, and low-side lobe level enabling the use of simple optical components like metal mirrors and HDPe lenses to focus the beam on a target.

With regard to the power level required to heat the workpiece 36, if the parison is manufactured of Pebax®, in order to bring the workpiece 36 from room temperature to 140° Celsius, and be able to blow a balloon, the required energy can be calculated according to the following. By way of example only, a typical parison tube can be, for example, 1 mm in an outer diameter, and 0.6 mm in the inner diameter, and have a length of 32 mm. The volume of such a tube therefore is 12.8 cubic mm. Taking a CP value of 1500 Joules per kilogram degree Celsius and a density of 1.1 grams/cm$^3$, this means that 2.54 Joules are required to heat the parison from room temperature to 140° Celsius. A commercial low power gyrotron, for example, that manufactured by Insight Product Co., which offers a 24 GHz continuous wave gyrotron with the output power being continuously regulated in the range of 0.1–3 kW by varying the electron beam voltage, up to a maximum of 12 kV, can be defocused roughly to its wavelength, i. e., 12 mm. Therefore when the parison is placed in the focus of the beam about $\frac{1}{12}$ of the beam will hit the target. Assuming a 50% absorption of the energy, this means that at 0.1 kW CW output power, it will take about 2.54 Joules/(100 (Joules))/24)=0.6 seconds to heat the parison.

Referring again to FIG. 1, not only can the apparatus 20 be used to manufacture balloons using microwave energy, but through the use of the temperature sensor 28 and the processor 26, a feedback loop is provided to thus enable the gyrotron 22 to be modulated based on the heated temperature of the mold 24 and/or workpiece 36. A suitable temperature sensor would be a model number OS 1592 Fast Response Infrared Fiber Optic Thermometer available through Newport Corporation, which gives about forty readings per second, or an infrared temperature sensor from Heitronics Corporation.

To control the power output of the gyrotron the pulse links of the input voltage on the cathode 54 could be adjusted. By doing so, it would be possible to, for example, operate a 10 kilowatt gyrotron at an average power level of 5 watts or even lower. If the end temperature should be controlled within plus or minus 2° F., the rise of the temperature should be less than 2° for every pulse in between the sensor readings. Therefore, there should be at least 60 readings in between 20 and 140° Celsius assuming a constant absorption coefficient of the polymer material as a function of the temperature. The update frequency of the Heitronics IR sensor is 200 Hz. Taking the earlier calculated 0.6 seconds to rise the parison 120° Celsius into account, which is 200° Celsius per second, and assuming for the time being a simplistic model of a linear rise, reading the IR sensor at 200 Hz will result in an accuracy of 1° Celsius. This demonstrates that it is not unrealistic with existing equipment and sensors to realize a control temperature rise in the parison to 140° Celsius with a precision of ±2° within less than 2 seconds.

In an alternative embodiment, the gyrotron beam could be defocused so that only a small percentage of the beam impinges upon the sample. For example, this could be done using a cylindrical lens. In so doing, a much smaller temperature rise could be achieved and the gyrotron could be stopped once the required temperature is reached. Similarly, the current of the cathode could be reduced thereby reducing the output power of the gyrotron. In a still further embodiment, use of a power splitter such as a polarizing splitter could be used to enable a 50/50 power split. Three of these such splitters in series would enable the power level to be reduced to 12.5%. One could also use the 50/50 splitting operation to do multiple balloon blowing at the same time. Defocusing the laser beam would also allow to heat multiple parisons at the same time.

Figure 4:
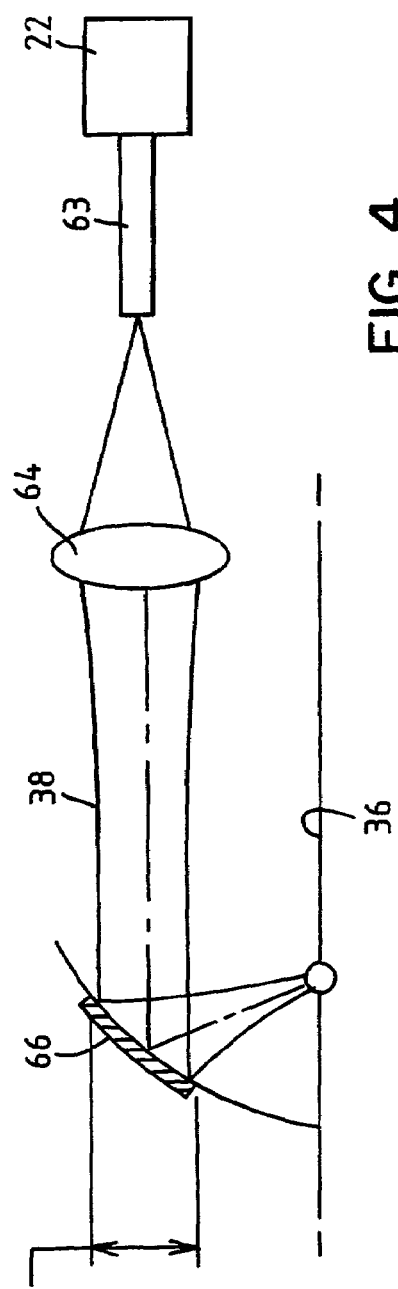
FIG. 4 is a diagrammatic representation of another alternative embodiment of a molding apparatus constructed in accordance with the teachings of the disclosure.
Figure 5:
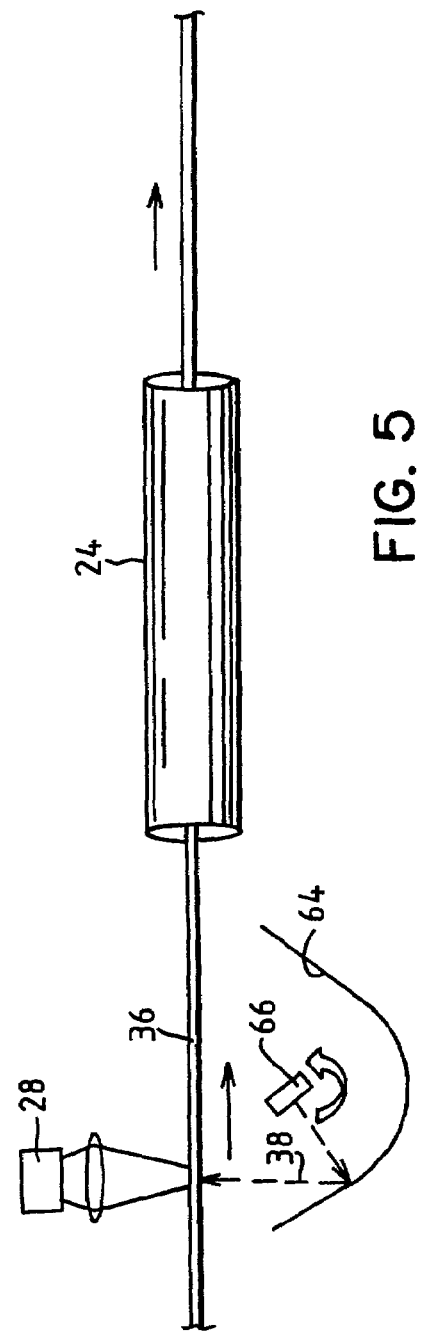
FIG. 5 is a flow chart depicting a sample sequence of steps which may be employed according to the method taught by the disclosure.

In order to focus the microwave output upon the workpiece 36 and provide an even heating profile across the balloon 34, the embodiments depicted in FIGS. 4 and 5 may be employed. In both embodiments, lenses are employed to focus the beam. For example, as shown in FIG. 4, the microwave source, which may be provided in the form of a gyrotron 22, directs microwave radiation through a waveguide 63 to a first lens 64, which in turn directs the focused microwave beam to a second lens 66. The first lens may be provided as an HDPE lens, while the second lens 66 may be an arcuate or focusing metallic mirror. Such lenses are readily, commercially available, such as through Farran Technology. One way of fabricating the balloon is to put the output of the circular wave guide 62 in the focal point of the HDPE lens in order to create a parallel beam and to direct that beam into a focusing mirror as shown in FIG. 4. Such operation will give a slightly inhomogeneous power distribution over the length of the polymer tube.

Alternatively, the beam could be scanned along a part of the tube to achieve a more uniform temperature distribution. This can be done by focusing the beam on a mirror which makes an angle, e. g., 45°, with the optical axis and which rotates around that optical axis as shown in FIG. 5. The beam is thereby scanned in a plane perpendicular with the optical axis. By putting the scanning mirror in the focal point of the parabolic mirror, a system is created wherein the beam can be scanned in one direction along the parison. This also allows a convenient way in which to integrate the infrared sensor. The microwave is focused by the scanning mirror and the focusing lens on a small part of the parison, e.g., on the order or the wavelength. The IR detector's position is perpendicular and is focused to the starting point of the scanned length on the parison.

As shown in FIG. 5 therein, a second lens 66 is a rotating lens which thus enables the focal point of the microwave energy to be not only focused, but moved across the axial length of the balloon 34. Moreover, the first lens 64 is provided in the form of a parabolic lens or mirror. The microwave beam is focused by the scanning mirror and the focusing lens on the small part of the parison. The infrared detector is positioned in a perpendicular direction and is focused to the starting point of the scan length on the parison. While the beam scans across the parison, the infrared sensor monitors the parison. As every point along the parison is receiving the same energy, all points will go to the same heated temperature. Once heated to the correct temperature, the parison is drawn quickly into the mold and the balloon can be blown. In another embodiment one could close a clamshell mold once the parison has reached its temperature. This would avoid having to move the parison. In the case of a pulse microwave system, a much higher pulse frequency is chosen achieving a significant overlap between two adjacent spots. In the case of a CW gyrotron even distribution is automatically obtained. It should be understood that there will be a drop in temperature while the parison is being transported into the mold, or during the closing of the mold, after the heating operation. This can be compensated for by monitoring the rate of this drop and, as the time of transportation is known, compensate for the drop in the heating cycle. This also allows a temperature profile to be achieved along the parison. For example, if it is desired to heat a certain section of the parison to a higher temperature, the infrared sensor can be focused at the high temperature and once the lowest temperature of the profile is reached, those pulses passing over the low temperature sections can be stopped.

Figure 7:
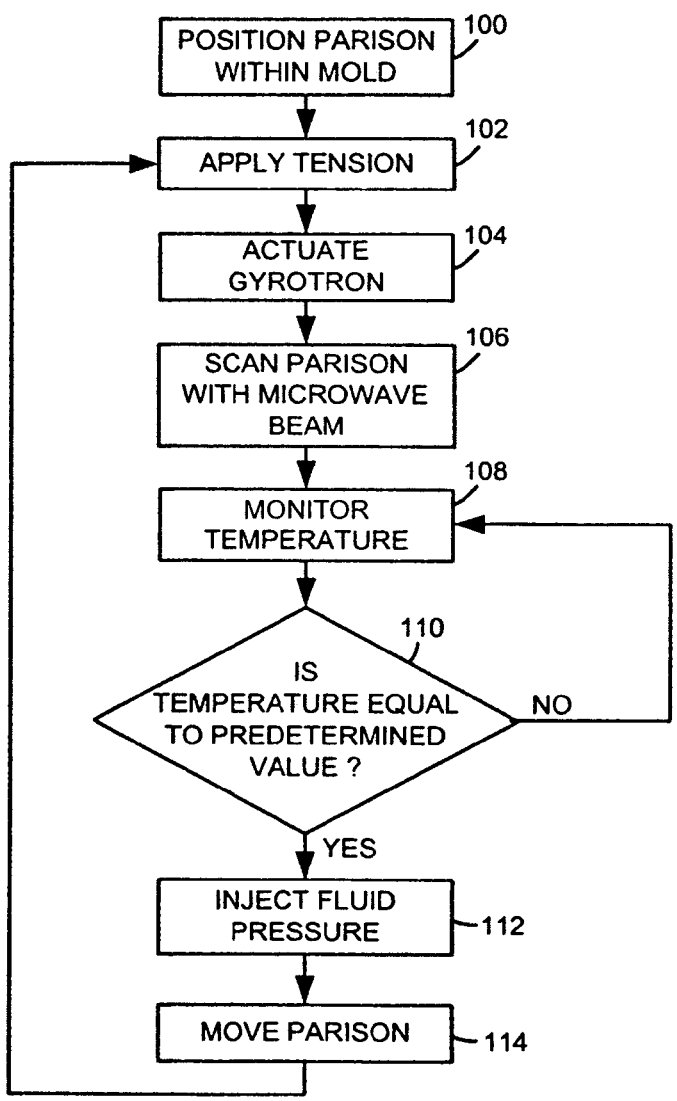
FIG. 7 is a flowchart depicting a sample sequence of steps which may be taken accordingly to the method disclosed herein.

Turning now to FIG. 7, a flowchart depicting s sample sequence of steps which may be taken according to the method of the disclosure is provided. As shown therein, a first step would be to position the parison workpiece 36 within the mold, as indicated by a step 100. Thereafter, if desired, the tensioners 30 and 32 may be actuated if desired to place the parison under tension during the heating process aided by step 102. The tensioners 30, 32 may be provided in a variety of readily available forms including, but not limited to, hydraulic or pneumatic clamps, rotating mandrels or spools, or the like. Once under tension, the gyrotron can be actuated, as indicated in step 104, with the microwave beam generated thereon being scanned across the parison as indicated by step 106. During such scanning, the temperature of the parison is continually monitored by the temperature sensor 28 as indicated in step 108. If the monitored temperature is equal to a predetermined level or within a predetermined range as is determined by the controller 26, as indicated in step 110, the compressor 39 can be actuated to direct pressurized air through the parison as indicated in step 112. Alternatively, the controller 26 may employ an algorithm wherein the gyrotron 22 is modulated in intensity based on the temperature readings. Thereafter, the parison can be moved through the mold 24 as indicated in step 114 and positioned to restart the process. Alternatively, if the monitored temperature is not within such a predetermined range, the temperature continues to be monitored until reaching such level.

Based on the foregoing, one of ordinary skill in the art will readily understand that the teachings of this disclosure can be employed to create a system for effectively and quickly molding medical devices such as balloon catheters.

What is claimed is:

1. A method of molding balloon catheters, comprising:
   positioning a parison within a mold, the mold having an interior cavity for forming a balloon;
   heating the parison using microwave energy for forming the balloon, the microwave energy being generated by a gyrotron;
   monitoring the temperature of the parison and adjusting the power of gyrotron based on the measured temperature; and
   directing fluid pressure into an interior of the parison when the parison reaches a predetermined temperature level, the fluid pressure expanding the parison into the interior cavity of the mold to form the balloon.

2. The method of claim 1, further including cooling the parison when in an expanded position within the mold.

3. The method of molding balloon catheters of claim 1, wherein the microwaves are generated at a frequency of between 10 to 110 gigahertz.

4. The method of molding balloon catheters of claim 1, wherein the microwaves have wavelengths within the range of about of 2.7 mm to about 30 mm.

5. The method of molding balloon catheters of claim 1, wherein the mold is made of a non-metallic material.

6. The method of molding balloon catheters of claim 5, wherein the non-metallic material is ceramic.

7. The method of molding balloon catheters of claim 2, wherein the cooling step is performed by engaging the parison with the mold.

8. The method of molding balloon catheters of claim 1, further including the step of stretching the parison while heating.

9. The method of molding balloon catheters of claim 1, wherein the heating step is performed by sweeping a microwave band across an axial length of the parison within the mold.

10. The method of molding balloon catheters of claim 9, wherein the microwave band is varied in strength as the band sweeps across the parison.

11. The method of molding balloon catheters of claim 9, wherein the microwave band is swept across the parison at a variable speed.

12. The method of molding balloon catheters of claim 10, wherein the microwave band strength is varied based on a sensed temperature within the mold.

13. The method of molding balloon catheters of claim 11, wherein the speed of the microwave band is varied based on a sensed temperature within the mold.

14. The method of molding balloon catheters of claim 1, further including the step of stretching the parison prior to the heating step.

15. The method of molding balloon catheters of claim 1, wherein the parison is heated within the mold.

16. A method of molding balloon catheters, comprising:
providing a parison of polymeric material;
subjecting the parison to microwave radiation generated by a gyrotron and being transmitted to the parison by way of at least two optical lenses comprising a focusing lens and a scanning lens;
monitoring the temperature of the parison;
injecting fluid pressure into the parison upon the temperature of the parison reaching a predetermined level to form a balloon; and
cooling the balloon.

17. The method of claim 16, wherein the microwave radiation is generated at a frequency within the range ot about 10 gigahertz to about 110 gigahertz.

18. The method of claim 16, wherein the microwave radiation is generated at a wavelength within the range of about 2.7 mm to about 30 mm.

19. The method of claim 16, wherein the parison is subjected to microwave radiation within a mold.

* * * * *